United States Patent [19]

Leonard

[11] 4,146,545

[45] * Mar. 27, 1979

[54] CYCLIC USE OF THALLIC OXIDE FOR PREPARING PROPYLENE OXIDE

[75] Inventor: John J. Leonard, Springfield, Pa.

[73] Assignee: Atlantic Richfield Company, Los Angeles, Calif.

[*] Notice: The portion of the term of this patent subsequent to Aug. 9, 1994, has been disclaimed.

[21] Appl. No.: 818,186

[22] Filed: Jul. 22, 1977

Related U.S. Application Data

[63] Continuation of Ser. No. 717,308, Aug. 24, 1976, abandoned, which is a continuation of Ser. No. 579,758, May 22, 1975, abandoned.

[51] Int. Cl.$^2$ ............................................ C07D 301/20
[52] U.S. Cl. ................................................. 260/348.24
[58] Field of Search ..................................... 260/348.24

[56] References Cited

U.S. PATENT DOCUMENTS

| | | | |
|---|---|---|---|
| 3,436,409 | 4/1969 | Hill et al. | 260/348.24 |
| 3,641,067 | 2/1972 | Kruse | 260/348.24 |

FOREIGN PATENT DOCUMENTS

| | | |
|---|---|---|
| 2255298 | 7/1975 | France. |
| 19770 | 6/1972 | Japan. |
| 13104 | 2/1974 | Japan. |

OTHER PUBLICATIONS

Kruse et al., J. Org. Chem., vol. 36, No. 8 (1971) pp. 1154–1155.

P. Schindler, Chimia (Switzerland) vol. 11 (1957) pp. 164–166.

*Primary Examiner*—Norma S. Milestone
*Attorney, Agent, or Firm*—John R. Ewbank; John C. Martin, Jr.

[57] ABSTRACT

In an aqueous alkaline solution having a pH greater than 11.9, thallous isobutyrate is oxidized by air at a temperature within a range from about 90° to about 250° C. to prepare a slurry of thallic oxide from which thallic oxide can be recovered. The alkaline isobutyrate solution can be treated with carbon dioxide under pressure to form a carbonate salt and isobutyric acid, which can be solvent extracted from the aqueous system using any hydrophobic solvent as extractant. Such isobutyric acid can be employed in a 30 percent aqueous solution at 90°–150° C. to dissolve thallic oxide and to prepare thallic triisobutyrate. This aqueous solution of thallic triisobutyrate can be employed for the oxidation of an organic compound susceptible to oxidation to desirable partially oxidized organic compounds. Gaseous propylene can be bubbled through a liquid reaction mixture containing water, an organic solvent miscible with water, and thallic trialkanoate to prepare gaseous propylene oxide. The carbonate salt can be thermally decomposed to regenerate an alkaline metal hydroxide and carbon dioxide. The availability of this novel preparation of thallic oxide makes feasible the recycling of most components, so that the thallium ion is an intermediate useful for the oxidation of an organic compound indirectly using the oxygen of air through such cyclic processing of the thallium ion.

2 Claims, No Drawings

CYCLIC USE OF THALLIC OXIDE FOR PREPARING PROPYLENE OXIDE

RELATED APPLICATIONS

U.S. Pat. No. 4,031,196, issued June 21, 1977 to J. J. Leonard from Ser. No. 717,309 filed Aug. 24, 1976 for Preparing Aqueous Alkaline Slurry of Thallic Oxide, benefited from ancestor Ser. No. 579,758 filed May 22, 1975, as does this continuation of Ser. No. 717,308 filed Aug. 24, 1976, each of said related cases being deemed here reiterated.

FIELD OF THE INVENTION

This invention relates to the preparation of thallic oxide from an aqueous solution containing thallous ion, to the oxidation of organic compounds by aqueous solutions of thallic ion and to recycle procedures for indirectly using the oxygen of air for the oxidation of an organic compound; for example, oxidizing propylene to propylene oxide using thallium ion as the intermediate.

PRIOR ART

Grinstead U.S. Pat. No. 3,048,636 and British Pat. No. 1,100,806 describe the oxidation of unsaturated organic compounds with solutions of thallic salts.

Kruse U.S. Pat. No. 3,641,067 describes contacting gaseous propylene with a liquid reaction mixture containing water, an organic solvent miscible with water, and thallic trialkanoate (e.g., thallic acetate or thallic butyrate) to form gaseous propylene oxide. Dioxane, tetrahydrofuran, tertiary butanol, and dimethylformamide are among the suggested solvents. Electrolytic regeneration of the thallous to thallic state is suggested.

Japanese Patent Publication No. 49-13104 describes a Tanaka proposal for using air to oxidize thallous chloride to thallic chloride in the presence of acetic acid and chloride salts such as potassium chloride, lithium chloride, sodium chloride and in the presence of corresponding acetate salts, and the contacting of gaseous propylene with a liquid reaction mixture containing water, an organic solvent miscible with water, and said mixture of acetic acid, acetate salts, chloride salts, and thallic chloride to form gaseous propylene oxide.

A considerable variety of publications disclose the use of thallic triacetate and/or other thallic compounds in liquid reaction mixtures containing water for oxidizing organic compounds selectively to desired organic compounds. Most of the investigations have been of a scholarly nature because electrolytic regeneration of thallous to thallic has been contemplated as an appropriate approach for the inorganic oxidation portion of the cycle.

There has been a long-standing demand for a process permitting efficient use of thallic ion for oxidation of an organic compound and permitting efficient recycling of the thallium component.

SUMMARY OF THE INVENTION

In accordance with the present invention, gaseous propylene is contacted with a liquid reaction mixture containing water, an organic solvent miscible with water, and thallic trialkanoate to form gaseous propylene oxide, and the thallium trialkanoate is prepared by leaching particles of thallic oxide with a hot aqueous alkanoic acid, and the thallic oxide is prepared by the oxidation of a thallous alkanoate in an aqueous solution having a pH greater than 11.9 by the introduction of an oxygen-containing gas into such system at a temperature range from about 90° to about 250° C.

The nature of the invention is further clarified by refermce to a plurality of examples.

EXAMPLES 1–4

A quantity of about 400 cc of aqueous alkaline solution is supplied to a titanium autoclave having a magnetic stirrer. The aqueous solution contains 0.19 molar thallous acetate. The oxygen containing gas contacts the stirred solution to oxidize the thallous ion to the thallic ion. The gas pressure was 300 psi of nitrogen and 300 psi of oxygen. The aqueous system contains the concentration of sodium necessary to obtain the indicated pH. In a series of preparations, the yield of thallic oxide was measured (the $Tl_2O_3$ being separated by filtration and its purity confirmed by analysis) to determine the effect of variations in the duration of the treatment and variations in initial pH. No measurable difference in pH occurred during the reaction. The results of this series of preparations are shown in Table 1. In Control A, the pH of the aqueous solution was only 11.5, with a significant loss in yield of $Tl_2O_3$ compared to $Tl_2O_3$ at a pH of 12.5.

Table 1

|  | molarity [NaOH] | pH | hrs. | % yield |
|---|---|---|---|---|
| Control A | 0.003 | 11.5 | 0.5 | 1.30 |
| Example 1 | 0.03 | 12.5 | 0.5 | 10.00 |
| Example 2 | 0.3 | 13.5 | 0.5 | 52.00 |
| Example 3 | 3.0 | 14.5 | 0.5 | 74.00 |
| Example 4 | 3.0 | 14.5 | 2 | 100.00 |

Such data show that oxygen can oxidize thallous ion to thallic ion at 150°C., at a rate of commercial interest if the pH is greater than 11.9. By a series of tests it is shown that the temperature must be maintained within a range from 90° to 250° and the initial thallium ion concentration in the aqueous composition must be at least 0.05 molar and desirably is less than 3 molar. The alkanoate ion concentration must be at least equal to the thallium ion concentration. The thallic oxide product is not merely insoluble in the reaction product, but also forms in a particle size suitable for separation by centrifuging or filtration. Such separability of a precipitate by filtration (it being herein assumed that if commercial filtration is manageable, then centrifuging is also manageable) is remarkable because hot aqueous alkaline solutions containing 3 molar sodium hydroxide at a pH such as 14.5 tend to disperse many precipitates in a colloidal form not susceptible to commercial filtration. It is sometimes advantageous to cool the reaction mixture prior to filtration, to wash the thallic oxide filter cake with dilute (e.g., pH 9) sodium hydroxide until the filtrate has a pH essentially the same as the wash liquid, and to dry the recovered thallic oxide.

EXAMPLES 5–6

A 500 cc titanium autoclave was charged with 100 cc of aqueous alkaline composition containing a controlled concentration of thallous isobutyrate, and the autoclave was pressurized at 600 psig with an equal mixture of nitrogen and oxygen. The pressurized mixture was agitated while being heated to and maintained at a reaction temperature of 200°C., for a controlled period of time, thus permitting the oxygen gas to oxidize the thallous isobutyrate. Barium hydroxide was the alkaline material. Data relating to some preparations are shown in Table 2.

Table 2

| Code | [Tl$^+$] molarity | [Ba(OH)$_2$] molarity | pH | hrs. | % yield |
|---|---|---|---|---|---|
| Ex. 5 | 0.095 | 0.14 | 13.3 | 2 | 94 |
| Ex. 6 | 0.19 | 1.4 | 14.2 | 2 | 85 |

The thallic oxide was separated from the reaction product by filtration.

EXAMPLE 7

An aqueous solution of filtrate from the thallic oxide separation step was processed for salvaging both the isobutyric acid and the barium component. Such filtrate is transferred to a pressurized extraction apparatus in which dibutyl ether was the hydrophobic solvent employed to extract isobutyric acid from the aqueous system. Carbon dioxide at about 600 psig is effective in converting the soluble barium hydroxide to insoluble barium carbonate and/or barium bicarbonate and in converting barium isobutyrate to butyric acid. Before, during, or after (preferably after) the extraction of the butyric acid, the barium carbonate and/or barium bicarbonate precipitate is recovered from the aqueous system.

By a series of tests it was established that the organic acid recovery by extraction with a hydrophobic solvent was manageable with acetic acid, better with propionic acid, and still better with alkanoic acids of the formula RCO$_2$H having 3 or 4 carbons in the R group. Isobutyric acid has certain advantages because of its combination of advantageous partition coefficients, (hydrophobic solvent, aqueous solution partition) boiling point, and related properties. About 99 percent of isobutyric acid has been recovered from a solution derived from a barium bicarbonate process by using ethyl ether as the hydrophobic solvent extractant for a day when the carbon dioxide pressure was essentially atmospheric pressure.

The barium carbonate is recovered, such as by filtration of the raffinate from the solvent extraction step. Such barium carbonate (and/or barium bicarbonate is calcined to generate carbon dioxide and to provide barium oxide. By dissolving the barium oxide in water an aqueous solution of barium hydroxide is prepared for recirculation to the thallic oxide preparation step.

The isobutyric acid is separated from the extractant by distillation. An aqueous solution of isobutyric acid containing about 33 percent (and assuredly between 20 percent and 45 percent) by weight water is prepared and heated to about 110°C., (and assuredly between 90° and 150° C.), which solution dissolves the separated particles of thallic oxide (recycled from the alkaline oxidation step). A solution of thallic triisobutyrate having a concentration within the range from 0.05 molar to 3 molar is thus prepared. Preferably the concentration of thallium trialkoate does not exceed 1 molar.

Such solution of thallic triisobutyrate is employed to oxidize an organic compound to a desirable partially oxidized compound, such as the oxidation of gaseous propylene to gaseous propylene oxide. The reaction of gaseous propylene is conducted to about 70° C., in a reaction mixture comprising about 70 percent tetrahydrofuran as a solvent, and the space rate is very large because the propylene is bubbled into the bottom of the reaction mixture, and the propylene oxide vapors (together with the vapors of acetone and/or other by-products) are withdrawn from the overhead.

Isobutylene glycol, ethylene glycol, cyclohexanone, and related partially oxidized organic compounds can be prepared using thallic trialkanoate as the oxidizing agent, this invention being concerned primarily with recycling the thallium in an effort to minimize net consumption of chemicals in any use of thallium ion for oxidation to a desired partially oxidized organic compound.

Cyclohexene is oxidized to cyclohexanone in the aqueous solution of thallium triisobutyrate resulting from the leaching of thallic oxide, no tetrahydrofuran or additional water being necessary.

EXAMPLE 8

By a series of tests, the appropriate limits are established for practicing the methods of previous examples. Prior literature indicates that the organic compound susceptible to oxidation may be an aldehyde, olefin, tertiary hydrocarbon (e.g., cumene), or other material which can be oxidized to a desirable partially oxidized organic compound.

In accordance with the present invention, the concentration of thallium in the aqueous composition must be within the range from 0.05 to 3 moles per liter of aqueous system both in the formation of the propylene oxide and in the formation of thallic oxide particles. Sufficient alkanoic acid ion, the R group of the RCO$_2^-$ anion having from 1 to 4 carbon atoms, must be present to justify discussion of thallium trialkanoate, but other solvents and/or anions can be present. A solvent miscible with water must be present in the liquid contacting gaseous propylene to form a gas comprising propylene oxide.

The desired organic product is separated from the residual aqueous mixture, which now contains thallous alkanoate. Such thallous alkanoate composition is transferred to the alkaline oxidation zone in which the thallium ion concentration is maintained within the range from 0.05 to 3 molar. The aqueous composition comprising thallous alkanoate is modified by the adding of metal hydroxide to provide an aqueous composition having a pH greater than 11.9, (thus having a minimum hydroxyl ion concentraton of 0.01 molar) desirably a pH of about 14.5, the concentration of hydroxyl ion preferably being about 3 molar but less than 5 molar. The metal hydroxide is a soluble metal hydroxide of a metal selected from the group consisting of lithium, sodium, potassium, calcium, strontium, barium, and mixtures thereof.

The alkaline system having the pH above 11.9 and 0.05–3.0 molar thallous alkanote is heated to a temperature within the range from 90° to 250°C., and contacted with an oxygen containing gas for a few hours to convert the thallous alkanoate to thallic oxide particles of sufficient size to be separable from the alkaline system by filtration. It is surprising that filterable particles of Tl$_2$O$_3$ can be formed in an aqueous system having a pH higher than 11.9, inasmuch as such alkaline solutions generally favor formation of colloidal precipitates which are not readily filterable. The Tl$_2$O$_3$ particles are filtered (or centrifuged) from the alkaline oxidation reaction mixture, and after washing, transferred to the leaching step.

The filtrate from such Tl$_2$O$_3$ separation step is substantially free from thallium ion but does contain water, metal hydroxide, and metal alkanoate. Such filtrate is treated with carbon dioxide to form the metal bicarbonate and/or metal carbonate, and to form the alkanoic acid. Extraction of such carbonated system with a hydrophobic solvent (ethyl ether or butyl ether are two examples illustrating that a wide boiling point range of hydrophobic solvents are suitable) permits separation of the alkanoic acid from the metal salt containing aqueous solution.

The metal oxide can be prepared by subjecting the metal salt to an elevated temperature at which carbon dioxide is evolved. Such step of preparing a metal oxide from a metal bicarbonate and/or metal carbonate is adequately described in prior literature and requires no further clarificaton. The recovered metal oxide can be dissolved in water to provide an aqueous system comprising metal hydroxide, suitable in the alkaline oxidation step.

Distillation may be employed to separate the alkanoic acid from the hydrophobic organic solvent employed as extractant. Such recovered alkanoic acid is employed to prepare an aqueous solution containing from 20 percent to 45 percent water and from 55 to 80 percent alkanoic acid, which solution can be employed to leach particles of thallic oxide (recirculated from the alkaline oxidation zone via a washing zone). The leaching temperature must be within the range from 90° to 150° C. The thus prepared aqueous solution of thallic trialkanoate is recirculated to the step of contacting gaseous propylene to prepare a withdrawn gas stream containing gaseous propylene oxide. The thallic trialkanoate is employed in preparing a liquid reaction mixture containing 0.05 to 3.0 molar thalium trialkanoate.

Because the regulations governing concentrations of chemicals in waste streams are becoming more strict than in earlier decades, it is important to design chemical methods to permit recirculation of most components so that the net consumption of most chemicals is minimized. Thallium ion has been a useful research tool but it has not been used significantly for commerical oxidation of organic compounds partly because of the absence of a satisfactory method of oxidizing the thallous ion with air to prepare recoverable particles of $Tl_2O_3$.

In its broader aspects, the present invention features the method of preparing propylene oxide, which method includes the steps of: contacting gaseous propylene with a liquid reaction mixture containing water an organic solvent miscible with water, and thallic trialkanoate to oxidize gaseous propylene to gaseous propylene oxide and to prepare a liquid mixture containing an aqueous alkanoic acid solution of thallous alkanoate, said alkanoic acid corresponding to the formula $RCO_2H$, the R of said alkanoic acid having from 1 to 4 carbon atoms, and the concentration of thallium ion in said liquid reaction mixture being at least 0.05 molar but less than 3 molar; withdrawing a gas stream from said liquid mixture, said withdrawn gas stream containing gaseous propylene oxide, thereby providing a residual solution comprising an aqueous alkanoic acid solution containing thallous alkanoate; preparing an aqueous alkaline composition having a pH greater than 11.9, the hydroxyl ion concentration being within a range from 0.01 to 5 molar, said aqueous alkaline composition containing a hydroxide of a metal of the group consisting of lithium, sodium, potassium, calcium, strontium, barium, and mixtures thereof and said alkaline composition also comprising the thallous content of said residual solution comprising an aqueous alkanoic acid solution containing thallous alkanoate, the thallous ion concentration being within the range from 0.05 molar to 3 molar, and contacting said aqueous alkaline composition with an oxygen containing gas at a temperature within the range from 90° to 250°C., to prepare a composition containing precipitated filterable particles of thallic oxide; separating said composition containing precipitated filterable particles of thallic oxide to provide a filtrate solution and to provide separated particles of thallic oxide; treating said filtrate solution with carbon dioxide at superatmospheric pressure to prepare an acidic mixture, thereafter employing a hydrophobic organic solvent to extract alkanoic acid from said acidic mixture, and removing alkanoic acid from said hydrophobic organic solvent by distillation and adding water to said alkanoic acid for preparing an aqueous solution consisting essentially of alkanoic acid containing from 20 percent to 45 percent by weight water and from 80 percent to 55 percent by weight alkanoic acid, said alkanoic acid being derived from said residual solution comprising an aqueous alkanoic acid solution containing thallous alkanoate; and treating said separated particles of thallic oxide with said aqueous solution of alkanoic acid at a temperature within the range from about 90° to about 150°C., to prepare a regenerated aqueous solution of thallic trialkanoate for recirculation to the contacting of additional gaseous propylene.

A more specific embodiment of the invention can be described as the method of obtaining propylene oxide which includes the steps of: treating propylene in a reaction mixture comprising an aqueous solution containing tetrahydrofuran and thallic trialkanoate to prepare a reaction product mixture containing said propylene oxide and an aqueous alkanoic acid solution of thallous alkanoate, said alkanoic acid corresponding to the formula $RCO_2H$, the R of the alkanoic acid having from 1 to 4 carbon atoms, the the concentration of thallium ion being at least 0.05 molar but less than 3 molar, said treatment consisting of directing gaseous propylene into the liquid reaction mixture; separating said propylene oxide from said reaction product mixture to provide a residual aqueous alkanoic acid solution of thallous alkanoate, said separating consisting of withdrawing a gas stream from above the liquid reaction mixture; adding metal hydroxide of the group consisting of lithium, sodium, potassium, calcium, strontium, barium, and mixtures thereof to a solution of thallous alkanoate to provide an aqueous composition having a pH greater than 11.9, the thallous ion concentraton being at least 0.05 molar, but less than 3 molar, maintaining said aqueous composition at a temperature within the range from about 90° to about 250° C., contacting said aqueous composition with gaseous oxygen to oxidize the thallous ion to thallic ion and to form an insoluble thallic oxide precipitate and to prepare an aqueous solution containing metal alkanote; separating said aqueous solution containing metal alkanoate having a pH greater than 11.9 from said insoluble thallic oxide precipitate by centrifuging or filtration to provide a filtrate solution containing metal hydroxide and metal alkanoate and substantially free from thallium ion; treating said aqueous solution containing metal alkanoate with carbon dioxide at superatmospheric pressure to prepare a mixture of aqueous solution of alkanoic acid, a metal salt selected from the group consisting of metal bicarbonate, metal carbonate, and mixtures thereof; employing a hydrophobic organic solvent selected from the group consisting of ethyl ether and butyl ether to extract alkanoic acid from said mixture of the metal salt and aqueous solution of alkanoic acid to provide a residual aqueous mixture comprising metal salt; subjecting said metal salt to an elevated temperature at which carbon dioxide is evolved and to prepare a metal oxide and dissolving such metal oxide in water to regenerate the metal hydroxide for recirculation for preparation of additional basic solution; removing alkanoic acid from said hydrophobic organic solvent by distillation, and adding water to said alkanoic acid to provide an aqueous solution consisting essentially of from about 20 per cent to about 45 percent by weight water and from about 80 per cent to 55 percent by weight alkanoic acid; and treating said separated insoluble thallic oxide precipitate with said aqueous solution consisting of 80 per cent to 55 per cent alkanoic acid and 20 per cent to 45 per cent water at a temperature within the range from about 90° to about 150° C. to prepare a regenerated aqueous solution of thallic trialkanoate for reciculation to the treatment of additional propylene.

I claim:

1. In the method in which gaseous propylene is oxidized to gaseous propylene oxide by contacting a liquid reaction mixture in a reaction zone, said liquid reaction mixture containing water and thallic trialkanoate, the thallic ions of said thallic trialkanoate being reduced to thallous ions in said reaction zone, whereby the thallium content of the reaction zone comprises thallic ions and thallous ions, said thallic trialkanoate being derived from an alkanoic acid corresponding to the formula $RCO_2H$, the R of said alkanoic acid having from 1 to 4 carbon atoms, the improvement which consists of: recycling the thallium content from said reaction zone through a thallous conversion zone consisting of a basic aqueous composition having a pH greater than 11.9 and containing at least 0.05 but not more than 3 molar thallous ion, maintaining said basic aqueous composition at a temperature within the range from about 90° to about 250° C., and contacting said basic aqueous composition within said temperature range with gaseous oxygen to oxidize the thallous ion to thallic ion and to form precipitated particles of an insoluble thallic oxide, separating said precipitated particles of an insoluble thallic oxide from such thallous conversion zone, and recycling to said reaction zone thallic trialkanoate derived from said particles of an insoluble thallic oxide.

2. The method of preparing propylene oxide, which method includes the steps of:

(a) contacting gaseous propylene with a liquid reaction mixture containing water, and thallic trialkanoate to oxidize gaseous propylene to gaseous propylene oxide and to prepare a liquid mixture containing an aqueous alkanoic acid solution of thallous alkanoate, said alkanoic acid corresponding to the formula $RCO_2H$, the R of said alkanoic acid having from 1 to 4 carbon atoms, and the concentration of thallium ion in said liquid reaction mixture being at least 0.05 molar but less than 3 molar;

(b) withdrawing a gas stream from said liquid mixture, said withdrawn gas stream containing gaseous propylene oxide, thereby providing a residual solution comprising an aqueous alkanoic acid solution containing thallous alkanoate;

(c) preparing an aqueous alkaline composition having a pH greater than 11.9, the hydroxyl ion concentration being within a range from 0.01 to 5 molar, said aqueous alkaline composition containing a hydroxide of a metal of the group consisting of lithium, sodium, potassium, calcium, strontium, barium, and mixtures thereof and said alkaline composition also comprising the thallous content of said residual solution comprising an aqueous alkanoic acid solution containing thallous alkanoate, the thallous ion concentration being within the range from 0.05 molar to 3 molar, and contacting said aqueous akaline composition with an oxygen containing gas at a temperature within the range from 90° to 250°C., to prepare a composition containing precipitated filterable particles of thallic oxide;

(d) separating said composition containing precipitated filterable particles of thallic oxide to provide a filtrate solution and to provide separated particles of thallic oxide;

(e) treating said filtrate solution with carbon dioxide at super-atmospheric pressure to prepare an acidic mixture, thereafter employing a hydrophobic organic solvent to extract alkanoic acid from said acidic mixture, and removing alkanoic acid from said hydrophobic organic solvent by distillation and adding water to said alkanoic acid for preparing an aqueous solution consisting essentially of alkanoic acid containing from 20 percent to 45 percent by weight water and from 80 percent to 55 percent by weight alkanoic acid, said alkanoic acid being derived from said residual solution comprising an aqueous alkanoic acid solution containing thallous alkanoate; and (f) treating said separated particles of thallic oxide with said aqueous solution of alkanoic acid at a temperature within the range from about 90°C., to about 150°C., to prepare a regenerated aqueous solution of thallic trialkanoate for recirculation to the contacting of additional gaseous propylene.

* * * * *